United States Patent
Toraishi (12)

(10) Patent No.: US 6,701,976 B1
(45) Date of Patent: Mar. 9, 2004

(54) JIG FOR INJECTING FIXED AMOUNT OF INSULIN AND MANUFACTURING METHOD THEREOF

(76) Inventor: Kenichi Toraishi, 6-10-17, Nishijin, Sawara-ku, Fukuoka-City, Fukuoka-Prefecture (JP)

( * ) Notice: Subject to any disclaimer, the term of this patent is extended or adjusted under 35 U.S.C. 154(b) by 0 days.

(21) Appl. No.: 10/354,563

(22) Filed: Jan. 30, 2003

(51) Int. Cl.⁷ ................................................. B65B 1/04
(52) U.S. Cl. ........................... 141/21; 141/27; 604/208; 604/246; 604/220; 604/187
(58) Field of Search ................... 141/2, 18, 21, 141/27; 604/181, 187, 197, 198, 208, 211, 220, 235, 246

(56) References Cited

U.S. PATENT DOCUMENTS 4,252,159 A * 2/1981 Maki ........................... 141/27
5,993,423 A * 11/1999 Choi ........................... 604/155
6,006,798 A * 12/1999 Lindquist ..................... 141/27
6,623,459 B1 * 9/2003 Doyle ......................... 604/197

* cited by examiner

Primary Examiner—Steven O. Douglas
(74) Attorney, Agent, or Firm—Jordan and Hamburg LLP

(57) ABSTRACT

A jig for injecting a fixed amount of insulin includes: a main fixture (1) having upper and lower sandwiching portions for sandwiching and supporting an insulin injector from both sides, at upper and lower portions on the rear surface of the insulin injector; a screw fixing piece (4) formed by extending one side of upper sandwiching portions 2 of the main fixture 1 upward; and, outside of the piece 4 for fixing an appointed quantity of screws, an injection button upper-limit position setting piece (6) whose upper portion is bent inward and which is provided with a slit (7) opened at its lower part, and the injection-button upper-limit position setting piece (6) is made freely movable up and down by screw fixation to the screw fixing piece (4) by inserting screws (8) through the slit (7).

2 Claims, 4 Drawing Sheets

JIG FOR INJECTING FIXED AMOUNT OF INSULIN AND MANUFACTURING METHOD THEREOF

BACKGROUND OF THE INVENTION

The present invention relates to a jig for injecting a fixed amount of insulin and a manufacturing method thereof. In detail, it relates to a jig for injecting a fixed amount of insulin which can set the amount of insulin to be injected to a fixed amount by fixing, to an arbitrary position, a dial and, furthermore, an injection button of an insulin injector which moves an injection button up and down by a turn of a dial and in which the amount of insulin to be injected is determined according to the position of the injection button, and a manufacturing method thereof.

DESCRIPTION OF THE PRIOR ART

A diabetic patient injects/receives a hypodermic injection of a certain fixed amount of insulin, and the amount of insulin is appropriately increased and decreased depending on the condition and examination findings.

Therefore, as an insulin injector for injecting insulin by an amount according to each patient and his/her condition, there exists an insulin injector as shown in FIG. 5. Namely, as shown in FIG. 5, the insulin injector has a dial 101 on the front central part and employs a method wherein an injection button 102 located on the dial 101 is moved up and down by a turn of the dial 101 and is set to a certain position, an injection needle 103 is inserted under the skin, and the injection button 102 is depressed, whereby insulin in a cartridge 104 arranged below the dial 101 is dosed by a fixed amount according to the height of the injection button 102, that is, the graduation of the dial 101.

In greater detail, by turning the dial 101 on the front central part clockwise, the injection button 102 located on the dial 101 rises according to the turning degree, and when the dial 101 is stopped at a certain fixed graduation, the injection button also stops at a certain fixed height, and the amount of insulin in the cartridge 104 to be dosed when the insulin injector is thereafter fitted to a human body, an injection needle 103 is inserted under the skin, and the injection button 102 is depressed to the lower limit corresponds to the graduation on the dial 101 and, furthermore, the amount of injection.

Although an insulin injector which employs a method wherein, as mentioned above, the amount of insulin to be injected is increased and decreased according to the increase and decrease in graduation of the dial is satisfactory for ordinary diabetic patients, inconveniences occur in the following cases: 10–20% of diabetic patients have decreased vision and, therefore, have difficulty in turning and adjusting the dial to a graduation which they desire. Furthermore, 5–10% of diabetic patients have a decreased grip or a hand tremor, therefore, when they try to turn and adjust the dial to a desirable graduation, they cannot accurately adjust the dial because of passing over or an insufficient turn.

Accordingly, for such diabetic patients with decreased vision or a hand tremor, the above-described conventional insulin injector has never been easy to use, and by means thereof, a required amount of insulin has not been accurately injected, either.

SUMMARY OF THE INVENTION

It is an object of the present invention to provide a jig for injecting a fixed amount of insulin which can fix the dial at a fixed graduation so that not only ordinary diabetic patients but also diabetic patients with decreased vision or a hand tremor can inject insulin by an injection amount required for him/herself, and moreover, it is an object to provide a method for manufacturing a jig for injecting a fixed amount of insulin.

In order to achieve the above-described objects, a jig for injecting a fixed amount of insulin of the present invention is a jig for fixing a dial of an insulin injector which has a dial on the front central part and which injects insulin in a cartridge arranged below the dial by an appointed amount by, by a turn of the dial, moving an injection button located on the dial up and down for setting to a certain position and by depressing the injection button, comprising: a main fixture having upper and lower sandwiching portions for sandwiching and supporting an insulin injector from both sides, at upper and lower portions on the rear surface of the insulin injector; a screw fixing piece formed by extending one side of the upper sandwiching portions of the main fixture upward with a required quantity of screw grooves cut open; and outside of the screw fixing piece, an injection-button upper-limit position setting piece whose upper portion is bent inward and which has a slit opened at the lower part, wherein the injection-button upper-limit position setting piece is made freely movable up and down by screw fixation to the screw fixing piece by inserting screws through the slit.

In some cases, the above-described injection-button upper-limit position setting piece is attached to a position closer to one side of the main fixture. In such a case, screw grooves are also cut open at a position closer to one side of the main fixture. And in this case, the part of the main fixture where the screw grooves are cut open concurrently serves as a screw fixing piece.

Herein, the above-described insulin injector moves the injection button up and down by a turn of the dial located on the front central part, and the further the dial is turned clockwise, the higher the position of the injection button becomes, and the higher the position of the injection button is, the greater the amount of insulin to be dosed when the injection button is depressed becomes.

Moreover, in the jig for injecting a fixed amount of insulin of the present invention, since the upper portion of the injection-button upper-limit position setting piece is bent inward, this bent portion comes into contact against the upper surface of the injection button and stops the injection button from further rising. Moreover, since the injection-button upper-limit position setting piece employs a method wherein screws are inserted through its slit and the front ends of these screws are fixed by a screw fixing piece, the screws can be loosened and the injection-button upper-limit position setting piece itself can be moved up and down, therefore, the vertical position of the bent portion of the injection-button upper-limit position setting piece can be freely changed. Accordingly, the upper limit of the injection button, that is, the turning degree of the dial can be freely changed, and according thereto, the amount of insulin to be dosed can be freely changed.

In addition, a method for manufacturing a jig for injecting a fixed amount of insulin to achieve the above-described objects is a method for manufacturing a jig for fixing a dial of an insulin injector which has a dial on the front central part and which injects insulin in a cartridge arranged below the dial by an appointed amount by, by a turn of the dial, moving an injection button located on the dial up and down for setting to a certain position and by depressing the injection button, comprising the steps of: forming a main fixture having upper and lower sandwiching portions for sandwiching and supporting an insulin injector from both sides, at upper and lower portions on the rear surface of the insulin injector; forming a screw fixing piece formed by extending one side of the upper sandwiching portions of the main fixture upward with a required quantity of screw grooves cut open; and forming, outside of the screw fixing piece, an injection-button upper-limit position setting piece whose upper portion is bent inward and which has a slit opened at the lower part, wherein the injection-button upper-limit position setting piece is made freely movable up and down by screw fixation to the screw fixing piece by inserting screws through the slit.

According to this manufacturing method, on one side of the upper sandwiching portions of the main fixture, a screw fixing piece is formed in a manner extending upward with a required quantity of screw grooves cut open, therefore, the main fixture and screw fixing piece can be integrally fabricated, and for example, if the material thereof is metal, by carrying out bending subsequent to press-forming, fabrication can be easily carried out at a low price.

The aforementioned is a case where the material of the jig for injecting a fixed amount of insulin of the present invention is metal, however, it may be plastic in addition to metal, and if the material is plastic, injection molding is normally carried out after a mold is prepared.

DETAILED DESCRIPTION OF PREFERRED EMBODIMENT

Figure 1:
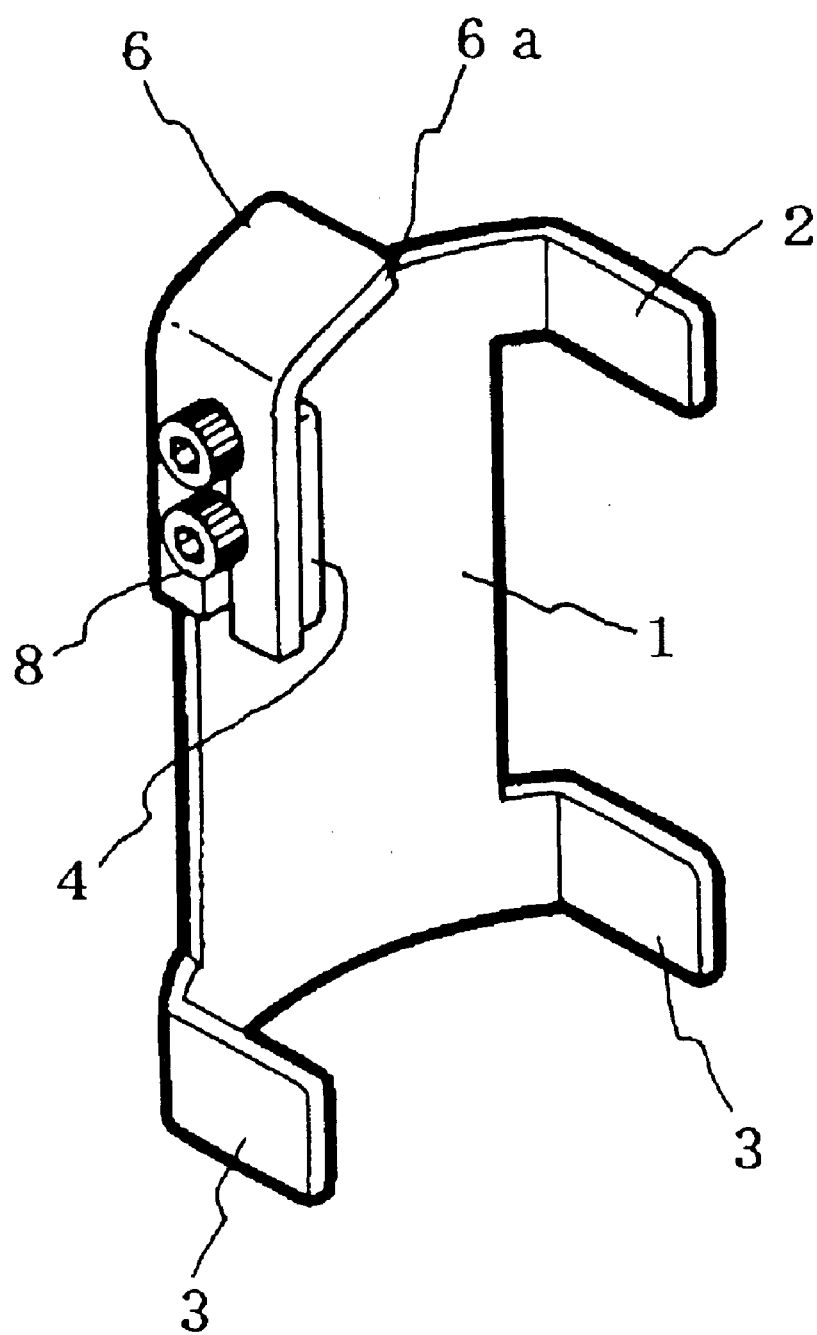
FIG. 1 is a perspective view of a jig for injecting a fixed amount of insulin according to the present invention.
Figure 5:
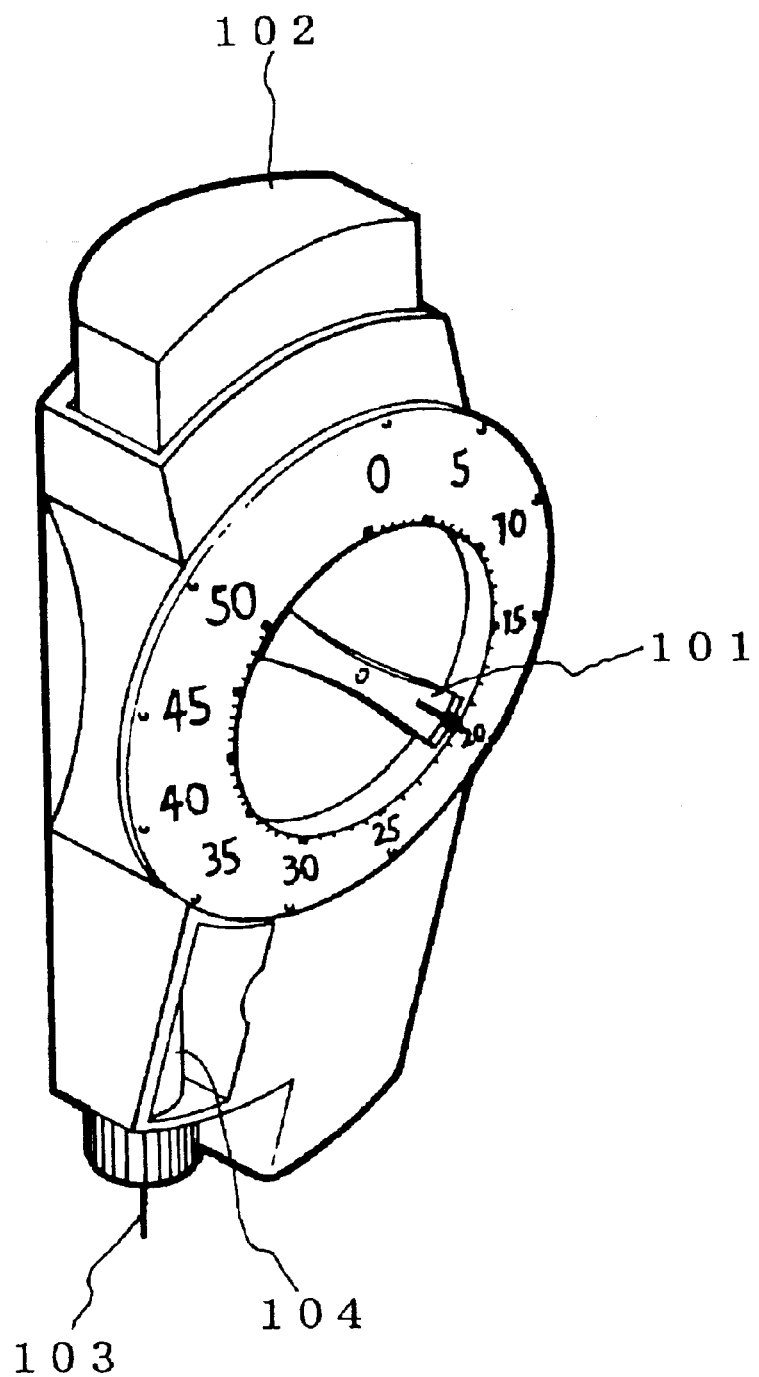
FIG. 5 is a perspective view of a conventional insulin injector.

An example of a jig for injecting a fixed amount of insulin to which the present invention has been applied is shown in FIG. 1. In this jig for injecting a fixed amount of insulin, upper sandwiching portions 2 and 2 and lower sandwiching portions 3 and 3 are formed, respectively, on both sides of the upper and lower portions of a main fixture 1, and by these upper and lower sandwiching portions, the conventional insulin injector shown in FIG. 5 is sandwiched and supported from its rear surface.

Herein, since the width and shape of the upper sandwiching portions 2 and 2 and lower sandwiching portions 3 and 3 are determined according to an insulin injector to be sandwiched and supported thereby, these are appropriately determined depending on the width and shape of a to-be-sandwiched portion of the insulin injector to which the jig for injecting a fixed amount of insulin of the present invention is attached.

Figure 2:
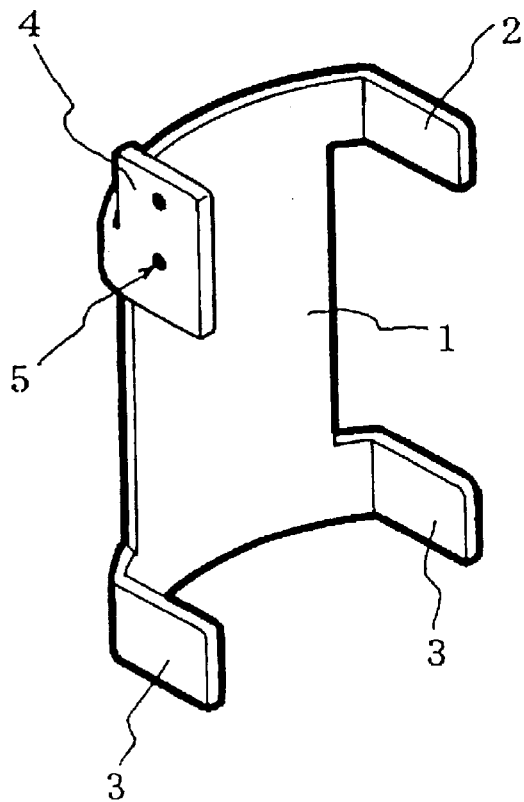
FIG. 2 is a perspective view of a main fixture and a screw fixing piece portion of a jig for injecting a fixed amount of insulin according to the present invention.

The main fixture 1 of this jig for injecting a fixed amount of insulin shown in FIG. 1 has a shape to follow the rear-surface shape of an insulin injector to which the same is attached by sandwiching and holding, and a slightly curved shape is shown in FIG. 1. A screw fixing piece 4 is, in FIG. 1, formed by extending the left side of the upper sandwiching portion 2 to its upper portion and in this screw fixing piece 4, a required quantity of screw grooves 5 are cut open as shown in FIG. 2.

Although the quantity of the thread grooves is not particularly limited, at least two screw grooves are preferably provided because these screw grooves 5 are used to fix an injection-button upper-limit position setting piece 6 at a desirable position (which will be described later in detail).

Figure 3:
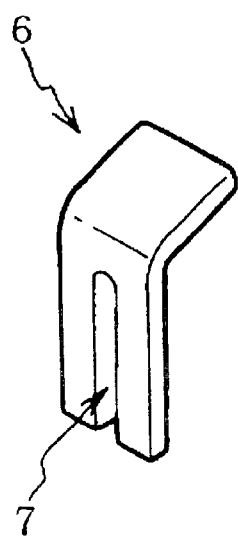
FIG. 3 is a perspective view of an injection button-upper-limit position setting piece of a jig for injecting a fixed amount of insulin according to the present invention.

On the outside of the above screw fixing piece 4, an injection-button upper-limit position setting piece 6 as shown in FIG. 3 by itself is abutted, and by inserting screws 8 through a slit opened at the lower half portion of the injection-button upper-limit position setting piece 6 and tightening the screws 8, the injection-button upper-limit position setting piece 6 can be fixed to the screw fixing piece 4. Accordingly, the height of an inward bent portion 6a of the upper portion of the injection-button upper-limit position setting piece 6 can be arbitrarily changed by moving the injection-button upper-limit position setting piece 6 up and down. Herein, the up-and-down movement of the injection-button upper-limit position setting piece 6 can be carried out by moving the injection-button upper-limit position setting piece 6 up and down along the slit 7 after loosening the screws 8 and then tightening the fixing screws 8 after fixing the same at a desirable position.

As mentioned above, the screws 8 preferably have, since they are tightened and loosened, a shape where the operation can be easily carried out, and, for example, as shown in FIG. 1, screws which have a hexagonal concave portion in the central part of its head and which can be loosened and tightened by a hexagon wrench inserted in said concave part are suitable.

By setting the bent portion 6a of the injection-button upper-limit position setting piece 6 to a certain fixed height as such, a degree by which the dial turns and, furthermore, a height to which the injection button rises are determined (which will be described later), thus a fixed amount of insulin can be dosed.

Furthermore, since the lower surface of the bent portion 6a of the upper portion of the injection-button upper-limit position setting piece 6 abuts against the injection button for preventing the injection button from rising further, it is preferable that the lower-surface shape meets the upper-surface shape of the injection button as much as possible, and since the central part of the upper surface of the injection button of a conventional insulin injector is normally curved upward so as to have a convex shape, the angle created between the vertical part of the injection-button upper-limit setting piece 6 and bent portion 6a is provided as approximately 115° in FIG. 1 and FIG. 3.

Figure 4:
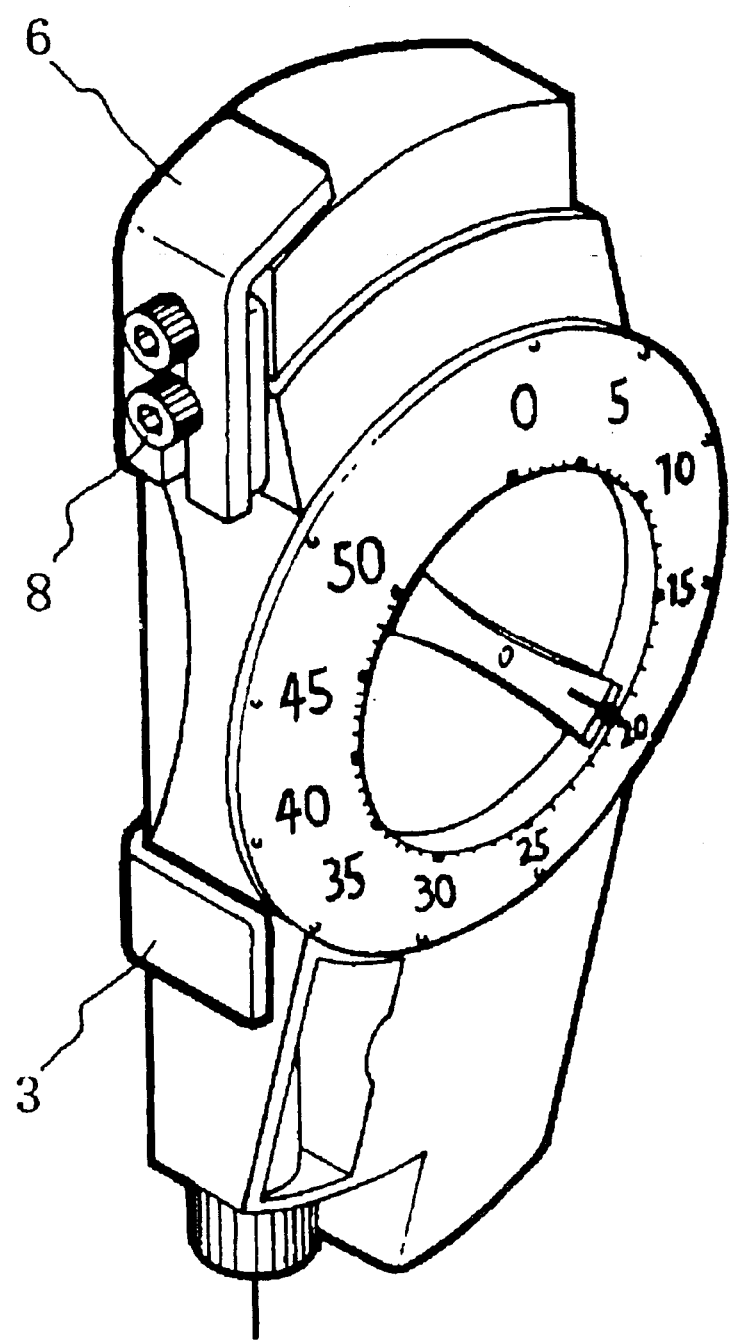
FIG. 4 is a perspective view of a jig for injecting a fixed amount of insulin according to the present invention, which has been attached to a conventional insulin injector.

In FIG. 4, shown is an explanatory view of a jig for injecting a fixed amount of insulin according to the present invention, which has been attached to a conventional insulin injector. The jig for injecting a fixed amount of insulin is fitted to the rear surface of the insulin injector and is securely fixed by the upper sandwiching portions 2 and 2 and the lower sandwiching portions 3 and 3.

Namely, the main fixture 1 (which does not appear in FIG. 4) is directly abutted against the rear surface of the insulin injector and holds the insulin injector in a clasping manner by the upper sandwiching portions 2 and 2 and the lower sandwiching portions 3 and 3.

Then, before or after this jig for injecting a fixed amount of insulin is attached to the conventional insulin injector, the vertical position of the injection-button upper-limit position setting means 6 is set to a desirable height.

Depending on the vertical position of this injection-button upper-limit position setting piece 6, the upper limit of the injection button and, furthermore, the turning degree of the dial are determined. Namely, in a conventional insulin injector, to which a jig for injecting a fixed amount of insulin of the present invention is to be attached, has a configuration wherein, as shown in FIG. 5, as a dial located at the front surface center is turned clockwise, the scale increases and concurrently therewith, an injection button located on the dial rises, and when the dial is stopped at a position, the injection button also stops at a certain height, and by a certain amount corresponding to the graduation pointed at this time by the dial, insulin is dosed when the injection button is depressed. Accordingly, if the height of the injection-button upper-limit position setting piece 6 is determined as a certain position in such a condition as shown in FIG. 4, the position of the bent portion 6a is also determined. In this condition, when the dial of the insulin injector is turned clockwise, the injection button also rises according thereto, however, this injection button stops because it cannot rise any further when the upper surface is abutted against the bent portion 6b of the injection-button upper-limit position setting piece 6, therefore, the dial cannot be turned any further.

As mentioned above, since the amount of insulin to be dosed has been determined according to the graduation of the dial and, furthermore, the rising degree of the injection button, the amount of insulin prepared for dosing when the dial is turned clockwise until it stops is determined as a certain fixed amount.

Adjustment of the height of this injection-button upper-limit position setting piece 6 can be correctly performed not by a diabetic patient him/herself but by a medical care provider or a care provider.

This is because, as mentioned above, many diabetic patients have decreased vision, a weak grip, or a hand tremor, such patients cannot easily adjust the height of the injection-button upper-limit position setting piece 6 and furthermore, incorrect adjustment easily occurs.

In addition, the amount of insulin to be dosed is determined according to each patient and his/her condition, however, in terms of a specific patient, since the amount of insulin to be dosed is not changed each day and is normally a fixed amount for a fixed period, once the injection-button upper-limit position setting piece 6 is set to a certain height by a medical care provider or a care provider, this is used for the fixed period without change.

After completion of vertical position setting of the injection-button upper-limit position setting piece 6, the insulin injector dial is turned clockwise as much as it can turn. Accordingly, the injection button rises, the upper surface thereof is abutted against the bent portion 6a of the injection-button upper-limit position setting piece 6, and the dial stops at a position where the injection button does not rise any further.

FIG. 4 illustrates a dial stopped at a graduation of 20, and the position where this dial stops when being turned is determined depending on the vertical position of the injection-button upper-limit position setting means 6.

After the dial and, furthermore, the injection button are fixed at a certain fixed position as such, the insulin injector is fitted to a human body, the injection needle is inserted under the skin, and the injection button is depressed to the lower limit, namely, until the graduation of the dial becomes 0, whereby insulin in a cartridge is dosed by a predetermined amount.

Furthermore, in the aforementioned manufacturing method, the step for forming a main fixture 1 having upper and lower sandwiching portions for sandwiching and supporting an insulin injector from both sides and the step for forming a screw fixing piece 4 by extending one side of the upper sandwiching portions of the main fixture 1 upward with a required quantity of screw grooves cut open have been described as separate steps, however, both these steps may be carried out by one step. This is because, since one of the upper sandwiching portions is extended upward and becomes a screw fixing piece 4, the main fixture 1 and the screw fixing piece 4 can be manufactured as an integral object.

In this case, if, for example, the material of the jig for injecting a fixed amount of insulin of the present invention is metal, a method can be considered as an example, wherein a main fixture 1 and a screw fixing piece 4 are press-formed as an integrally connected material, then bending for forming sandwiching portions is carried out.

Herein, the material of a jig for injecting a fixed amount of insulin is not limited to metal and may be plastic, and in such a case, injection molding is preferably performed after preparing a mold, as mentioned in the foregoing.

In addition, the material of a jig for injecting a fixed amount of insulin of the present invention may be either metal or plastic, while, preferably, the jig for injecting a fixed amount of insulin can be attached by, as shown in FIG. 4, fitting the same to the rear surface of a conventional insulin injector and by sandwiching the insulin injector by the upper sandwiching portions 2 and 2 and lower sandwiching portions 3 and 3, therefore, the material preferably has elasticity to some degree. This is because if the jig for injecting a fixed amount of insulin is an elastic material, by fitting the same to the rear surface of an insulin injector and pressing the same by some degree of force, the upper and lower sandwiching portions are slightly expanded and the jig is attached to the insulin injector, and after being attached, this jig stably holds the insulin injector by its own restoring force.

Even if a jig for injecting a fixed amount of insulin of the present invention is made of plastic, at least the screws 8 are preferably made of metal, if possible. Since the screws 8 are loosened and tightened a great number of times, a high degree of strength is required therein. Accordingly, even if portions other than the screws 8, namely, the main fixture 1, screw fixing piece 4, and injection-button upper-limit setting piece 6 are made of plastic, at least the screws 8 are preferably made of metal with high strength.

Moreover, in general, the majority of currently used insulin injectors are disposable and, accordingly, it is preferable that a jig for injecting a fixed amount of insulin to which the present invention has been applied can also correspond thereto. Namely, it is preferable that, when the jig for injecting a fixed amount of insulin is attached to an insulin injector, the injection-button upper-limit position setting piece 6 always has an identical height, and this poses no inconvenience, because a jig which can nearly satisfy therewith can be formed by a contrivance in a method of forming the upper and lower sandwiching portions, and even if the height of the injection-button upper-limit position setting piece 6 is not aligned when the jig for injecting a fixed amount of insulin is attached to an insulin injector, the height can be adjusted by loosening the screws 8 at this time, as well. Namely, the dial always stops at a desirable position of the graduation, and a fixed amount of insulin can be dosed by depressing the injection button.

In either case where an insulin injector to be attached to a jig for injecting insulin of the present invention is a disposable type or a non-disposable type, since the jig for injecting a fixed amount of insulin of the present invention is used in a manner attached to an insulin injector of a certain fixed form, once the jig for injecting a fixed amount of insulin of the present invention is fabricated to meet an objective insulin injector and once the injection-button upper-limit setting piece 6 is set to a certain position, the same height is maintained with virtually no shift.

As has been described in detail in the above, according to a jig for injecting a fixed amount of insulin of the present invention, by adjusting the vertical position of the injection-button upper-limit position setting piece in advance or after the jig for injecting a fixed amount of insulin to a conventional insulin injector, the dial can be stopped at a graduation where insulin suitable for each patient whom insulin is to be dosed, therefore, the diabetic patient who doses insulin can dose a correct amount of insulin by turning the dial clockwise until the dial stops, inserting the injection needle in this condition, and depressing the injection button to the lower limit.

Accordingly, if the height of the injection-button upper-limit position setting piece is adjusted in advance by a medical care provider or a care provider so that the dial stops at a determined position, even patients with decreased vision, as reported in 10–20% of diabetic patients, or patients with a deteriorated grip or a hand tremor, as reported in 5–10% of the same, can easily dose a required fixed amount by only turning the dial clockwise completely until it stops, while it is unnecessary for the patients to adjust a graduation each time by means of their poor eyesight and, furthermore, their hands which do not fully function because of a deteriorated grip or a hand tremor.

In addition, according to a method for manufacturing a jig for injecting a fixed amount of insulin of the present invention, in either case where a metal is used or plastic is used as a material thereof, an accurate product whose manufacturing method is easy can be obtained.

What is claimed is:

1. A jig for injecting a fixed amount of insulin for fixing a dial of an insulin injector which has a dial on the front central part and which injects insulin in a cartridge arranged below the dial by an appointed amount by, by a turn of the dial, moving an injection button located on the dial up and down for setting to a certain position and by depressing the said injection button, comprising:

a main fixture having upper and lower sandwiching portions for sandwiching and supporting an insulin injector from both sides, at upper and lower portions on the rear surface of the insulin injector;

a screw fixing piece formed by extending one side of the upper sandwiching portions of the main fixture upward with a required quantity of screw grooves cut open; and outside of said screw fixing piece, an injection-button upper-limit position setting piece whose upper portion is bent inward and which has a slit opened at the lower part, wherein the injection-button upper-limit position setting piece is made freely movable up and down by screw fixation to the screw fixing piece by inserting screws through the slit.

2. Method for manufacturing a jig for injecting a fixed amount of insulin for fixing a dial of an insulin injector which has a dial on the front central part and which injects insulin in a cartridge arranged under the dial by an appointed amount by, by a turn of the dial, moving an injection button located on the dial up and down for setting to a certain position and by depressing the said injection button, comprising the steps of:

forming a main fixture having upper and lower sandwiching portions for sandwiching and supporting an insulin injector from both sides, at upper and lower portions on the rear surface of the insulin injector;

forming a screw fixing piece formed by extending one side of the upper sandwiching portions of the main fixture upward with a required quantity of screw grooves cut open; and forming, outside of said screw fixing piece, an injection-button upper-limit position setting piece whose upper portion is bent inward and which has a slit opened at the lower part, wherein the injection-button upper-limit position setting piece is made freely movable up and down by screw fixation to the screw fixing piece by inserting screws through the slit.

* * * * *